United States Patent [19]
Behr

[11] Patent Number: 5,891,925
[45] Date of Patent: Apr. 6, 1999

[54] DIAGNOSTIC METHOD FOR ASSESSING THE SERUM CHOLESTEROL RESPONSE TO LOW DIETS

[75] Inventor: Stephen R. Behr, Westerville, Ohio

[73] Assignee: Abbott Laboratories, Abbott Park, Ill.

[21] Appl. No.: 884,601

[22] Filed: Jun. 27, 1997

[51] Int. Cl.⁶ .......................... A61K 31/70; A61K 33/00; A61K 31/19; A23L 1/00
[52] U.S. Cl. ............................................ 514/824; 514/909
[58] Field of Search ...................................... 514/824, 909

[56] References Cited

U.S. PATENT DOCUMENTS

| 5,308,832 | 5/1994 | Garleb et al. | 514/2 |
| 5,393,784 | 2/1995 | Richardson | 514/561 |
| 5,639,471 | 6/1997 | Chait et al. | 424/439 |

FOREIGN PATENT DOCUMENTS

| 0367724A | 5/1990 | European Pat. Off. . |
| 0462398A | 12/1991 | European Pat. Off. . |
| 0756827A | 2/1996 | European Pat. Off. . |
| WO 9508349A | 3/1995 | WIPO . |
| WO 97 13415 A | 4/1997 | WIPO . |

OTHER PUBLICATIONS

National Cholesterol Education Program (NCEP), "Live Healthier, Live Longer: Lowering Cholesterol for the Person w/ Heart Disease", NIH Pub. No. 96–3805, Sep. 1996.
National Heart, Lung, and Blood Institute (NHLBI), "Recommendations Regarding Public Screening for Measuring Blood Cholesterol", NIH Pub. 95–3045, Sep. 1995.
National Heart, Lung and Blood Institute (NHLBI), "Step by Step: Eating to Lower Your High Blood Cholesterol", NIH Pub. No. 94–2920, Aug. 1994.
Schaefer et al. *FASEB*, vol. 8(4):A452(2620), Mar. 15, 1994.
Davidson et al. *FASEB*, vol. 8(4):A453(2621), Mar. 15, 1994.
Adult Treatment Panel II "Second Report of the Expert Panel on Detection, Evaluation, and Treatment of High Blood Cholesterol in Adults", National Cholesterol Education Program, vol. 89, No. 3, Mar. 1994.

Chait et al., "Rationale of the Diet–Heart Statement of the American Heart Association" The AHA Medical/Scientific Statement, vol. 88, No. 6, Dec. 1993. (pp. 3008–3028).

Ross Products Medical Nutritional Handbook, "*A Total Commitment To Enteral Nutrition*", May 1996.

Ross Products Sales Literature, "*Ensure® Light*", Sep. 1996.

Anticancer Research, vol. 14, 1994, pp. 1451–1455, XP002035801, C. Cangiano, et al., "Cytokines, Tryptophan and Anorexia in Cancer Patients Before and After Surgical Tumor Ablation".

*Primary Examiner*—Howard C. Lee
*Attorney, Agent, or Firm*—Thomas D. Brainard

[57] ABSTRACT

A diagnostic method for assessing how a hypercholesterolemic person's serum cholesterol level will respond to a low total fat and saturated fat diet. The method involves defining a target cholesterol level, measuring a baseline level, feeding for a term of 3–25 days a NCEP Step I diet of which at least 50% of the caloric intake is provided by a fortified, low-fat nutritional product, and comparing the post term cholesterol level to the defined goal to see if the target is met. If the target is met, the person is predicted to respond to dietary intervention. If the target is not met, the person is deemed a non-responder and is considered for drug therapy. A fortified, low-fat nutritional product supplies in about 1000 kcal (i) 100% of the adult RDI for vitamins and minerals; and (ii) total fat, saturated fat and cholesterol levels that are at or below the levels specified for a Step II diet. Preferably the total fat comprises 25% or less of total calories; and the saturated fat and cholesterol maximum levels are less than about 2–3% of total calories in the case of saturated fat, and less than about 30–50 mg per 1000 kcal in the case of cholesterol.

28 Claims, 6 Drawing Sheets

DIAGNOSTIC METHOD FOR ASSESSING THE SERUM CHOLESTEROL RESPONSE TO LOW DIETS

This invention relates generally to diagnostic methods and, more particularly, to a method for assessing how a hypercholesterolemic person's serum cholesterol level will respond to a low total fat and saturated fat diet. The method is useful for rapidly, conveniently, accurately and economically differentiating those hypercholesterolemic persons who will respond satisfactorily to dietary intervention from those who will fail to respond satisfactorily.

BACKGROUND

Coronary Heart Disease (CHD) causes nearly 500,000 deaths per year and is the single leading cause of death in America today. Elevated serum cholesterol levels constitute a major modifiable risk factor for CHD, and the results of numerous large-scale clinical trials have convincingly demonstrated that lowering serum cholesterol reduces prevalence of fatal and non-fatal myocardial infarction as well as total mortality. The major ongoing public health effort to reduce coronary heart disease in the United States was sparked by the alarmingly high incidence of morbidity and mortality that resulted from this chronic disease. Because of this, there have been intensive efforts to develop new and more potent strategies to reduce risk factors for CHD. There are two major strategies for preventing CHD by lowering serum cholesterol. One is a patient based approach that seeks to identify individuals at high risk who will benefit from intensive intervention efforts. The goal of this approach is to detect, treat, and monitor high-risk individuals who have elevated serum cholesterol. The other strategy is the public health approach that attempts to lower serum cholesterol levels in the entire population by promoting changes in dietary habits and physical activity levels. These two strategies are complementary and both are incorporated in the National Cholesterol Education Program (NCEP) of the National Institutes of Health Second Report of the Expert Panel on Detection, Evaluation, and Treatment of High Blood Cholesterol in Adults updated recommendations for cholesterol management. This invention relates to the patient-based approach of identifying individuals at high risk for CHD.

Dietary intervention is the cornerstone of cholesterol lowering. Three major dietary factors contribute to high levels of serum cholesterol; these are a high intake of saturated fat, a high intake of dietary cholesterol, and an imbalance between calorie intake and energy expenditure leading to obesity. The NCEP has suggested the use of Step I and Step II Diet guidelines to assist the individual in modifying their diets. Step I and Step II Diets emphasize the choice of fruits, vegetables, grains, cereals, and legumes as well as poultry, fish, lean meats and low fat diary products instead of foods high in saturated fat and cholesterol, such as whole-milk dairy products and high-fat meats. The Step I and Step II Diets will be described later in the description. Thus, the primary aim of dietary intervention is to reduce CHD risk by decreasing intakes of saturated fat and cholesterol and by restoring appropriate calorie balance, while simultaneously promoting good nutrition.

Not all individuals are equally sensitive to dietary modification and some subjects will have high cholesterol levels that are inherently resistant to dietary modification. The mechanisms for this resistance are not completely understood. Because these individuals can not achieve the cholesterol-lowering goal despite good adherence to a Step I or Step II Diet, drug therapy may be the only effective treatment for their high serum cholesterol. For most subjects, at least 6 months of intensive dietary intervention and counseling should be carried out before considering drug therapy. Some subjects may even require 12 or more months of dietary intervention before considering drug treatment. This represents a delay in implementing an effective cholesterol-lowering regimen.

Thus, primary care physicians and their hypercholesterolemic patients lack a convenient, accurate, rapid and economic diagnostic method to determine how a person's serum cholesterol level will respond to the implementation of a cholesterol-lowering diet. A feature of the present invention is to provide such a diagnostic method.

SUMMARY OF THE INVENTION

The present invention relates to a method for quickly and conveniently differentiating those hypercholesterolemic persons who will respond to dietary intervention from those who will not. Thus, in a first aspect, the invention provides a method of predicting a hypercholesterolemic person's serum cholesterol response to a low-fat diet, comprising:

(a) defining a target serum total cholesterol level for said person;

(b) measuring said person's baseline serum total cholesterol level prior to dietary intervention;

(c) feeding said hypercholesterolemic person a diet that is a NCEP Step I Diet for term of about 3 to about 25 days; wherein about 50 to 100% of the caloric intake of said person is supplied by a fortified, low-fat nutritional product; and (d) at the end of said term, measuring said person's serum total cholesterol level and comparing it to the baseline level; wherein a decrease in total cholesterol to a level at or below said defined target level is predictive of response to dietary intervention.

The target serum total cholesterol level may be defined by a number of means, including defining it as a decrease of about 10% or more from baseline serum total cholesterol levels prior to diet intervention. Typically, the prediction can be made after a term of about 3 to about 14 days, more preferably about 5 to 10 days.

One hundred percent of said hypercholesterolemic person's caloric intake may be supplied by a complete nutritional product that meets the NCEP Step I guidelines. When less than 100% of the caloric intake is supplied by a fortified, low-fat nutritional product that meets the Step I guidelines, the remaining caloric intake is from conventional foods that fall under the NCEP Step I Diet guidelines.

In another aspect, the invention provides a method of identifying a hypercholesterolemic person who will fail to respond to a low-fat diet designed to lower serum total cholesterol level, said method comprising:

(a) defining a target serum total cholesterol level for said person;

(b) measuring said person's baseline serum total cholesterol level prior to dietary intervention;

(c) feeding said hypercholesterolemic person a diet that is a NCEP Step I Diet for term of about 3 to about 25 days; wherein about 50 to 100% of the caloric intake of said person is supplied by a fortified, low-fat nutritional product; and (d) at the end of said term, measuring said person's serum total cholesterol level and comparing it to the baseline level; wherein a failure to achieve a serum total cholesterol level at or below said target level is indicative of a person who will fail to respond to dietary intervention. The predefined target level and preferred terms are as above.

One hundred percent of said hypercholesterolemic person's caloric intake may be supplied by a complete nutritional product that meets the NCEP Step I guidelines. When less than 100% of the caloric intake is supplied by a fortified, low-fat nutritional product that meets the Step I guidelines, the remaining caloric intake is from conventional foods that fall under the NCEP Step I Diet guidelines. Other aspects of the invention are described throughout the application.

DETAILED DESCRIPTION OF THE INVENTION

A. LIPID BACKGROUND

Figure 1:
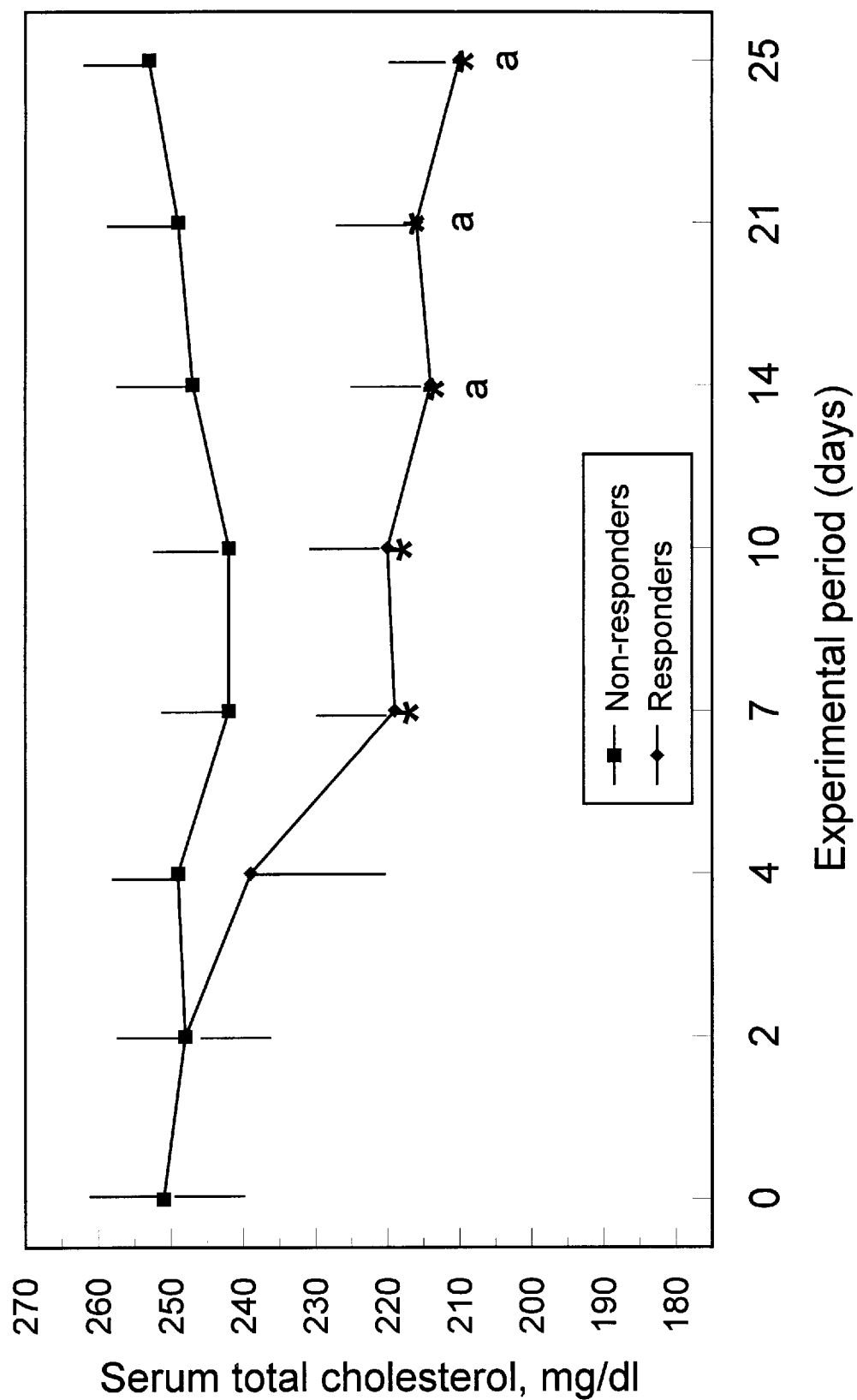
FIGS. 1 and 4 describe the changes in serum total cholesterol levels in responders and non-responders over a 25 or 14 day period as described in examples I and II, respectively.

Dietary cholesterol causes marked hypercholesterolemia and atherosclerosis in many laboratory animals, including non-human primates. Controlled metabolic studies indicate that dietary cholesterol raises the serum cholesterol level in many humans. The degree of rise, however, varies from person to person. There is evidence that dietary cholesterol augments the serum cholesterol raising action of saturated fat. Thus, a diet high in cholesterol contributes to the high LDL cholesterol levels of many high risk patients and thereby increases CHD risk. Dietary cholesterol is found only in animal products, especially in the same foods that are rich in saturated fats.

Cholesterol is a fat-like substance that is present in cell membranes and is a precursor of bile acids and steroid hormones. It consists of four carbon rings with a hydroxyl group at one end and a freely movable hydrocarbon tail at the other end. Cholesterol travels in the blood in non-covalent bound spherical complexes of lipids (triglycerides, phospholipids, free cholesterol and cholesterol esterified to fatty acids) and protein called "lipoproteins". The cholesterol level in the serum is determined partly by inheritance and partly by acquired factors such as diet, calorie balance and level of physical activity.

Three major classes of lipoproteins are found in the serum of a fasting individual, each of which contain cholesterol to varying degrees. The density of the lipoprotein complex is determined by its relative ratio of lipid and protein. The higher the ratio of protein to lipid, the higher the density. The higher the ratio of lipids to protein, the lower the density. Thus, the lipoproteins are classified according to density and by relative lipid and cholesterol loads.

Low-density lipoproteins (LDL) typically carry 60% to 70% of the total serum cholesterol and are directly correlated with risk for CHD. High-density lipoproteins (HDL) normally carry 20% to 30% of the total serum cholesterol and HDL levels are inversely correlated with CHD risk. Very-low-density lipoproteins (VLDL) carry 10% to 15% of the total serum cholesterol along with most of the triglyceride in fasting serum. VLDL are precursors of LDL, and some forms of VLDL appear to be atherogenic, producing degenerative changes in the arterial walls.

Fatty acids are hydrocarbon chains of various lengths, having a methyl group at one end and a carboxyl group at the other. If each intermediate carbon of the chain is covalently bound to two hydrogens, the fatty acid is classified as "saturated". The saturated fats include three major cholesterol-raising fatty acids, which have carbon chain lengths of 12 (lauric acid), 14 (myristic acid) and 16 (palmitic acid). The predominant effect of saturated fat is to raise LDL cholesterol levels. Foods rich in these three fatty acids are the primary targets for reduction in cholesterol lowering diets.

B. CLINICAL CLASSIFICATION AND FOLLOW-UP

The National Cholesterol Education Program (NCEP) guidelines suggest that serum total cholesterol be measured in all adults 20 years of age and over at least once very 5 years with HDL cholesterol being measured at the same time. Because most cholesterol in serum is contained in LDL, the concentration of total cholesterol in most persons is highly correlated with the concentration of LDL cholesterol. Initial testing for serum total cholesterol has several advantages: it is more readily available, it is less expensive, and it does not require that the individual be fasting. In individuals free of Coronary Heart Disease (CHD), total cholesterol levels of less than 200 mg/dL are classified as "desirable serum cholesterol"; those of 200 to 239 mg/dL as "borderline-high serum cholesterol"; and those of 240 mg/dL or greater as "high serum cholesterol". The threshold that defines high serum cholesterol (240 mg/dL) is a value above which risk for CHD rises more steeply. An HDL cholesterol level of less than 35 mg/dL is defined as "low", and a low HDL cholesterol level constitutes a CHD risk factor. Additional CHD risk factors include: males over the age of 45, females over the age of 55, family history of premature CHD, current cigarette smoking, hypertension, and diabetes mellitus.

For adults without evidence of CHD, initial assessment is based on total cholesterol and HDL cholesterol. Depending on the results and the presence or absence of other CHD risk factors, LDL measurement may also be indicted and may affect follow-up. Table 1, below, summarizes the National Cholesterol Education Program (NCEP) guidelines as follows: For individuals with "desirable serum cholesterol", the level of HDL cholesterol initially determines the appropriate follow-up. If HDL is less than 35 mg/dL, however, LDL levels determines follow-up. For individuals with "borderline-high serum cholesterol", the level of HDL cholesterol and the presence or absence of multiple other CHD risk factors initially determine the follow-up. However, if HDL is less than 35 mg/dL or if two other CHD risk factors are present, then LDL levels determine follow-up. For individuals with "high serum cholesterol", LDL cholesterol levels and the presence or absence of multiple other CHD risk factors determine the follow-up regardless of HDL level. Levels of LDL cholesterol of 160 mg/dL or greater are classified as "high-risk LDL cholesterol," those of 130 to 159 mg/dL as "borderline-high risk LDL cholesterol," and those of less than 130 mg/dL as "desirable LDL cholesterol."

One important aim of dietary intervention is to achieve the LDL cholesterol goal without the need for drugs. If maximally achievable dietary modification is inadequate to meet the LDL cholesterol goal, consideration will be given to adding drug therapy to dietary intervention. The NCEP recommended goals for LDL levels are as follows: for subjects with high-risk LDL cholesterol and fewer than two other CHD risk factors, the LDL cholesterol goal is less than 160 mg/dL; for subject mg/dL or more aesterol of 130 mg/dL or more and two or more CHD risk factors, the LDL cholesterol goal is less than 130 mg/dL; and for subjects with CHD and LDL cholesterol levels of greater than 100 mg/dL, the LDL cholesterol goal is 100 mg/dL or lower.

TABLE 1

| Cholesterol | HDL cholesterol | LDL Cholesterol | Appropriate Follow-Up |
| --- | --- | --- | --- |
| <200 mg/dL "Desirable" | >35 mg/dL | N/A | provide general educational material about dietary modification, physical activity, and other risk reduction activities; repeat total cholesterol and HDL cholesterol analysis in 5 years |
| | <35 mg/dL | <130 mg/dL | provide information on diet and exercise designed for the general population; reevaluate in 5 years |
| | | 130 to 159 mg/dL with fewer than two other CHD risks factors | give instructions in dietary modification and physical activity; reevaluate for risk status and lipoprotein profile in 1 year |
| | | 130 to 159 mg/dL with two or more CHD risks factors or ≧160 mg/dL | start and monitor a cholesterol-lowering diet |
| 200 to 239 mg/dL "Borderline" | >35 mg/dL and fewer than two other CHD risk factors | N/A | Provide instruction in dietary modification, physical activity and other risk-reduction activities; repeat total cholesterol and HDL cholesterol analysis in 1 to 2 years |
| | <35 mg/dL or two (or more) other CHD risk factors | <130 mg/dL | provide information on diet and exercise designed for the general population; reevaluate in 5 years |
| | | 130 to 159 mg/dL with fewer than two other CHD risks factors | give instructions on dietary modification and physical activity; reevaluate for risk status and lipoprotein profile in 1 year |
| | | 130 to 159 mg/dL with two or more CHD risks factors or ≧160 mg/dL | start and monitor a cholesterol-lowering diet |
| >240 mg/dL "High" | any | <130 mg/dL | provide information on diet and exercise designed for the general population; reevaluate in 5 years |
| | | 130 to 159 mg/dL with fewer than two other CHD risks factors | give instructions in dietary modification and physical activity; reevaluate for risk status and lipoprotein profile in 1 year |
| | | 130 to 159 mg/dL with two or more CHD risks factors or ≧160 mg/dL | start and monitor a cholesterol-lowering diet |

C. DIETARY INTERVENTION

In those individuals for whom dietary intervention is indicated, the general aim is to reduce elevated serum cholesterol while maintaining a nutritionally adequate eating pattern. Dietary intervention occurs in two steps designed to reduce progressively the intake of saturated fatty acids and cholesterol and to promote weight loss in patients who are overweight by eliminating excess total calories and increasing physical activity. The National Cholesterol Education Program's (NCEP's) eating pattern recommendation for the general public is similar in nutrient intake to the Step I Diet. Consequently, at the time of detection of high serum cholesterol, many individuals may already be adhering to the recommended diet. If the individual has not adopted the Step I Diet, this should be the first step of dietary intervention. If the individual is already adhering to the Step I Diet at the time of detection or if this diet proves inadequate to achieve the goals of dietary intervention, the individual should proceed to the Step II Diet.

TABLE 2

| Features | Step I Diet | Step II Diet | Average American Diet |
| --- | --- | --- | --- |
| total fat | ≦30% of calories | ≦30% of calories | 33% to 37% of calories |
| saturated fat | 8% to 10% of calories | <7% of calories | 13 to 17% of calories |
| cholesterol | <300 mg/day | <200 mg/day | 300 to 500 mg/day |

Total fat in both the Step I and Step II Diets should make up 30% or less of total calories (Table 2). Current total fat intake in the United States averages 33% to 37% of calories. Therefore, fat intake must be reduced by about one fifth to meet the target of 30% or less. The average subject will have to reduce saturated fat intake by about one third to adopt the Step I Diet; by about one half for the Step II Diet. The Step I Diet calls for an average intake of dietary cholesterol of less than 300 mg/day. A further restriction to less than 200 mg/day is recommended with the Step II Diet. A second authority with published guidelines to decrease risk of coronary heart disease include the American Heart Association. The NCEP "Step I diet" is identical to the American Heart Association's "prudent diet".

According to the NCEP guidelines, a minimum of 6 months of intensive dietary intervention and counseling should be carried out before evaluating the efficacy of diet intervention. For individuals who are hypercholesterolemic and who do not respond to diet modification, trying diet modification for 6 months and often longer represents a delay in pharmacological treatment of a major modifiable risk factor for CHD. Drug therapy should be considered as a supplement to dietary intervention when the total cholesterol goal is not reached.

D. DRUG THERAPY

Drug treatment should be considered for an adult subject who despite dietary intervention fails to achieve their target LDL cholesterol level. The goals of drug therapy are the same as those of dietary intervention. The thresholds set in the NCEP goals for consideration of drugs is not a point at which drugs are definitely required in all subjects. The physician's decision to proceed to drug therapy depends on the assessed risk of the subject, which in turn is based on the level of LDL and HDL cholesterol and the number and severity of other CHD risk factors. In subjects not considered to be a high risk for developing CHD over the next one or two decades, drug therapy often can be withheld or delayed.

Cholesterol lowering drugs are classified into the following major classes: bile acid sequestrants, nicotinic acid and HMG CoA reductase inhibitors. Other classes of drugs include fibric acid derivatives and probucol. Drug therapy is likely to continue for many years or a lifetime. Therefore, the decision to add drug therapy to the regimen should be made only after vigorous efforts at dietary intervention have not proven sufficient. Conversely, subjects who will not respond to dietary intervention should be identified as quickly as possible in order that suitable drug therapy be initiated.

E. THE INVENTIVE METHOD

The present invention provides a method of predicting a hypercholesterolemic person's cholesterol-lowering response to a low-fat diet. A hypercholesterolemic person is identified by a physician utilizing the National Cholesterol Education Program (NCEP) criteria described above. The NCEP criteria are the current standard of practice for risk assessment and definition of "hypercholesterolemia". It is understood that future updates to the guidelines may replace the current criteria.

Once the individual has been identified as hypercholesterolemic, the patient and physician must determine if dietary intervention will sufficiently lower the patient's risk of CHD (i.e. if the individual will be a "responder" or "non-responder" to dietary intervention.) They will decide upon the low-fat diagnostic diet suitable to the individual patient. The low-fat diet is obtained through replacement of between 50% and 100% of the total caloric requirement with a fortified, low-fat nutritional product that meets the Step II diet criteria. The remainder of the diet will consist of nonfat or low-fat foods self selected in accordance with a Step I or Step II diet (fat-free fruits, vegetables, grain and dairy products—as appropriate).

The term "nutritional product" includes but is not limited to these FDA statutory food categories: conventional foods, foods for special dietary uses, dietary supplements and medical foods. "Foods for special dietary uses" are intended to supply a special dietary need that exists by reason of a physical, physiological, pathological condition by supplying nutrients to supplement the diet or as the sole item of the diet. A "dietary supplement" is a product intended to supplement the diet by ingestion in tablet, capsule or liquid form and is not represented for use as a conventional food or as a sole item of a meal or the diet. A "medical food" is a food which is formulated to be consumed or administered enterally under the supervision of a physician and which is intended for the specific dietary management of a disease or condition for which distinctive nutritional requirements, based on recognized scientific principles, are established by medical evaluation.

As used herein, a "fortified, low-fat nutritional product" is defined as a nutritional product which, in a quantity sufficient to supply about 1000 kcal, provides: (i) 100% of the adult RDI for vitamins and minerals (hence "fortified"); and (ii) total fat, saturated fat and cholesterol levels that are at or below the levels specified for a Step II diet (hence "low-fat"). Since a typical "average" diet is based on about 2000 kcal per day, providing 100% of the RDI in half this caloric intake assures adequate vitamin and mineral intake without regard to the foods chosen to supplement the diet. This is important when only 50% of the calories are supplied by the fortified, low-fat nutritional product in accordance with the invention. Fortified, low-fat nutritional products used to replace 50% of the diet preferably are, but need not be, complete and balanced. Consequently, products from all the statutory food categories will fit this application. However, when 100% of the caloric intake is supplied by the fortified, low-fat nutritional product, a complete and balanced product is preferred. Complete and balanced nutritional products may additionally comprise fiber, trace and ultra trace elements in amounts designed to deliver a full daily requirement in about 2000 kcal.

The second requirement of a "fortified, low-fat nutritional product" is that the total fat, saturated fat and cholesterol levels that are at or below the levels specified for a Step II diet. For example, 1000 kcal of a fortified, low-fat nutritional product will provide no more than 30% of its total calories as total fat, no more than 7% as saturated fat and no more than about 100 mg as cholesterol (again assuming a 2000 kcal/day diet, 50% of which is supplied by the fortified, low-fat nutritional product). Preferably these levels are even lower. In a preferred embodiment, the total fat comprises 25% or less of total calories. Additionally, saturated fat and cholesterol maximum daily levels are preferably less than about half to one third of the Step II diet levels; i.e. less than about 2–3% of total calories in the case of saturated fat, and less than about 30–50 mg per 1000 kcal in the case of cholesterol.

A typical fortified, low-fat nutritional composition for this invention comprises about 10% to about 27%, usually about 13% to about 24% of calories as protein; about 43% to about 80%, usually about 50% to about 66% of calories as carbohydrate; and about 0% to about 30%, usually about 10% to about 30% of calories as fat subject to the Step II fat restrictions noted above. A liquid fortified, low-fat nutritional product has a caloric density of about 0.2 kcal/ml to about 2.0 kcal/ml, usually about 0.4 kcal/ml to about 1.6 kcal/ml. A solid fortified, low-fat nutritional product has a caloric density of about 75 kcal/oz to about 150 kcal/oz, usually about 85 kcal/oz to about 130 kcal/oz.

The compositions may also comprise unique ingredients known to have cholesterol-lowering activity such as but not limited to soy and other vegetable proteins, distinctive oils or oil blends, and soluble and insoluble dietary fiber.

The physical form of the fortified, low-fat nutritional product may be liquid, as in the case of ready to feed and concentrates; solid, such as powders and bars; or semi-solid, including but not limited to puddings, yogurts and frozen liquids. The different product forms may be used in combination to encourage compliance with the low-fat diagnostic diets.

The nutritional products used in the Examples happen to be complete liquid nutritional products representative of the compositions described above. The Ensure High Protein (Example I) is within the NCEP Step II guidelines, wherein an 8 oz. serving of the product provided 225 calories, 6 gm of total fat (24% of calories), 0.5 gm of saturated fat (2% of calories), less than 5 mg of cholesterol, 12 gm of protein, 31 gm of carbohydrates and at least 25% of the RDI for 25 vitamins and minerals. Ensure High Protein is commercially available from Ross Products Division of Abbott Laboratories (Columbus, Ohio). The complete liquid nutritional in Example II provided 65% of calories as carbohydrate, 14% of calories as protein, 24% of calories as total fat, 2% of calories as saturated fat and less than 5 mg of cholesterol per 8 fl. oz. can (supplying 225 kcal).

Those knowledgeable in the art of manufacturing liquid nutritionals may reference 1) U.S. Pat. No. 5,547,927 to Cope et al; 2) U.S. Pat. No. 5,416,077 to Huang et al; 3) U.S. Pat. No. 5,104,677 to Behr et al; 4) U.S. Pat. No. 4,921,877 to Cashmere et al; 5) U.S. Pat. No. 5,403,826 to Cope et al; 6) U.S. Pat. No. 5,221,545 to Borschel et al; 7) U.S. Pat. No. 5,223,285 to DeMichele et al; 8) U.S. Pat. No. 5,108,767 to Mulchandani et al; 9) U.S. Pat. No. 5,456,926 to Hill et al; and 10) U.S. Pat. No. 5,221,668 to Henningfield et al for production methods of liquid nutritionals. A more detailed composition is set forth in Example II.

An estimate of the adult patient's energy needs (total caloric requirement) may be calculated by the commonly used classic Harris-Benedict equation, modified for activity. The equation involves measurements of weight in kilograms, height in centimeters and age in years and generates an estimate of total caloric requirement. The minimum number of servings of the nutritional product to be consumed per day is determined by multiplying total caloric requirement by the percent of the calories being supplied by the nutritional product, dividing by total calories per serving of the nutritional and rounding up to the nearest whole number.

The term of the low-fat diagnostic diet is about 3 to about 25 days, with the understanding that the term could be extended due to individual circumstances. One would not expect the term to run longer than the typical 6 months of the current standard of practice self-selected low-fat diet intervention. At this point, the present invention would not provide the added benefit of rapid evaluation. The more preferred term is about 3 to about 14 days with the most preferred term being 5 to 10 days.

In order to practice the method of this invention, one measures serum lipid levels both at pre-diet intervention time point and at end of term time point. At least two measurements from two different days are preferred to assess accurately serum lipids at a specific time point. Fasting serum lipid measurements include but are not limited to total cholesterol, triglycerides and HDL cholesterol. Standard of practice analytical methods are used to obtain serum lipid values. As discussed previously, to the extent that changes in total cholesterol concentration highly correlate with changes in LDL concentration and inversely correlate with HDL concentration in most persons, these endpoints are considered equivalent measurements in determining response to a low-fat diet. The preferred cholesterol test is total cholesterol because it is more readily available, less expensive, and does not require that the subject be fasting.

Diet responsiveness is by definition a change in serum total cholesterol that accompanies a change in diet, and these responses are known to be normally distributed. As used herein, a "responder" is defined as a subject whose serum total cholesterol reproducibly decreases to a level at or below the predefined target at the end of the term. Well controlled studies in which subjects switch from a typical American diet to a Step I or Step II diet have reported individual responses ranging from a 30% decrease to a 10% increase in total cholesterol. In clinical practice, a reduction in total cholesterol of 10% or more is often considered to be clinically significant. Thus, a target level may conveniently, though not universally, be defined as a 10% or more decrease in the subject's baseline total serum cholesterol. Alternatively, a subject's target level may be defined by the NCEP recommended goals; or by the physician judgment based on the individual patient's unique circumstances. "Non-responders" are conversely defined as those subjects who fail to achieve the predefined target.

Recent studies by the present Applicants have indicated that low-fat diagnostic diets can rapidly, accurately, conveniently and economically predict the serum total cholesterol response to a low-fat diet. Furthermore, with non-responders being identified with much higher accuracy in both studies, an added value of the method lies in helping physicians more quickly determine which patients are candidates for drug therapy.

F. EXAMPLES

EXAMPLE I

Hypercholesterolemic subjects who were candidates for cholesterol-lowering dietary intervention according to National Cholesterol Education Program (NCEP) criteria, were fed Ensure High Protein (Ross Products Division of Abbott Laboratories) at 50% of total calories (Study BG34of 50% of tothe present study was to determine whether a diet of 50% of total calories as a liquid nutritional which meets the NCEP recommendations and 50% as NCEP recommended low-fat foods could distinguish between low-fat diet "responders" and "non-responders" in a 25 day period.

Subjects (23 women and 6 men) between the ages of 22 and 75 were selected from screening sessions. Subjects were included if they had serum total cholesterol levels greater than 200 mg/dL; fell under one of the three LDL cholesterol initiation level categories listed in Table 1; were omnivorous and consumed an average American diet; were in generally good health. The subjects were excluded if they had: bowel disease; known intolerance's or allergies to the ingredients in Ensure High Protein; hypoglycemia or diabetes mellitus; or if they participated in a drug treatment program for homozygous hypercholesterolemia or in a weight reduction program.

Twenty-one subjects were fed a diet composed of 50% of calories and greater than 90% of the protein intake from Ensure High Protein. The remainder of the diet consisted of nonfat foods self selected to be within a Step II diet (e.g. fat-free fruits, vegetables, grain and dairy products). Caloric need was determined by the Harris-Benedict formula, modified for activity. No fewer than four, 8 fl. oz. cans (900 kcal) were consumed per day. A reference group (N=8) continued consuming their normal diet. Fasting serum lipids and body weight were measured at day 0, 2, 4, 7, 10, 14, 21 and 25 in the twenty-one subjects consuming Ensure High Protein. In the eight reference subjects, fasting serum lipids were measured at days 0, 10 and 28. Fasting serum lipid measurements included total cholesterol (TC), triglycerides (TG) and HDL cholesterol (HDL-C). Cholesterol and TG were measured by the Monotest Cholesterol procedure and the GPO triglyceride procedure of Boehringer Mannheim adapted to automatic analysis using the Roche Cobas-Fara II Analyzer. HDL-C was measured following heparin and $Mn^{2+}$ precipitation. The laboratory was certified by CDC as a regional reference center for lipid analyses.

Based on food diary records, the typical total daily intake for the 50% Ensure High Protein group comprised about 15 to 17% of calories as total fat, about 1.7% of calories as saturated fats and less than 50 mg of cholesterol.

In contrast to the reference group, patients consuming 50% of their total caloric intake as Ensure High Protein had an average 10 mg/dL reduction in TC over the 25 day period when compared to levels before diet intervention. LDL cholesterol decreased 15 mg/dL (p=0.002), HDL-C decreased 6.6 mg/dL (p<0.001) compared to levels before diet intervention. The maximum TC response to the 50% Ensure High Protein diet occurred between 7 and 14 days after the initiation of the diet.

In this study, target levels were defined as a decrease in TC of at least 10% from baseline on two of the three final time points (day 14, 21 and 25). Based on this definition, five of the 21 (24%) 50% Ensure High Protein diet subjects were identified as "responders". Compared to pre-diet intervention, the "responder's" TC decreases were statistically significant after 7 days on the 50% diet and remained so at every time point until the end of the study. Four of the 5 responders had a greater than 10% decrease in their TC by day 10 resulting in an 80% correct identification of "responders". The changes in total cholesterol (mg/dL) levels in responders, n=5 (♦) and non-responders, n=16 (■) over a 25 day period of consuming 50% of total calories as Ensure High Protein are plotted in FIG. 1 [*=significantly different compared to day 0 (p<0.05); a=significantly different compared to non-responsive group (p<0.05)]. The mean change in serum cholesterol levels in the remaining "non-responders" (76%) group did not change significantly over the 25 days. Furthermore, seven of the 16 non-responders had 0% change from pre diet intervention. Only two of the 16 non-responders had a greater than 10% decrease in their TC by day 10 resulting in an 88% correct identification of "non-responders". Therefore, it was possible to identify correctly 80% of the responders and 88% of the non-responders by day 10, using 2 separate fasting serum cholesterol values.

TABLE 3

Number of Patients Correctly Identified

| | Early TC response avg. 7 and 10 day value | Equilibrium TC response after 14 day value | Accuracy |
|---|---|---|---|
| Responders | 4 | 5 | 80% |
| Non-responders | 14 | 16 | 88% |

Figure 2:
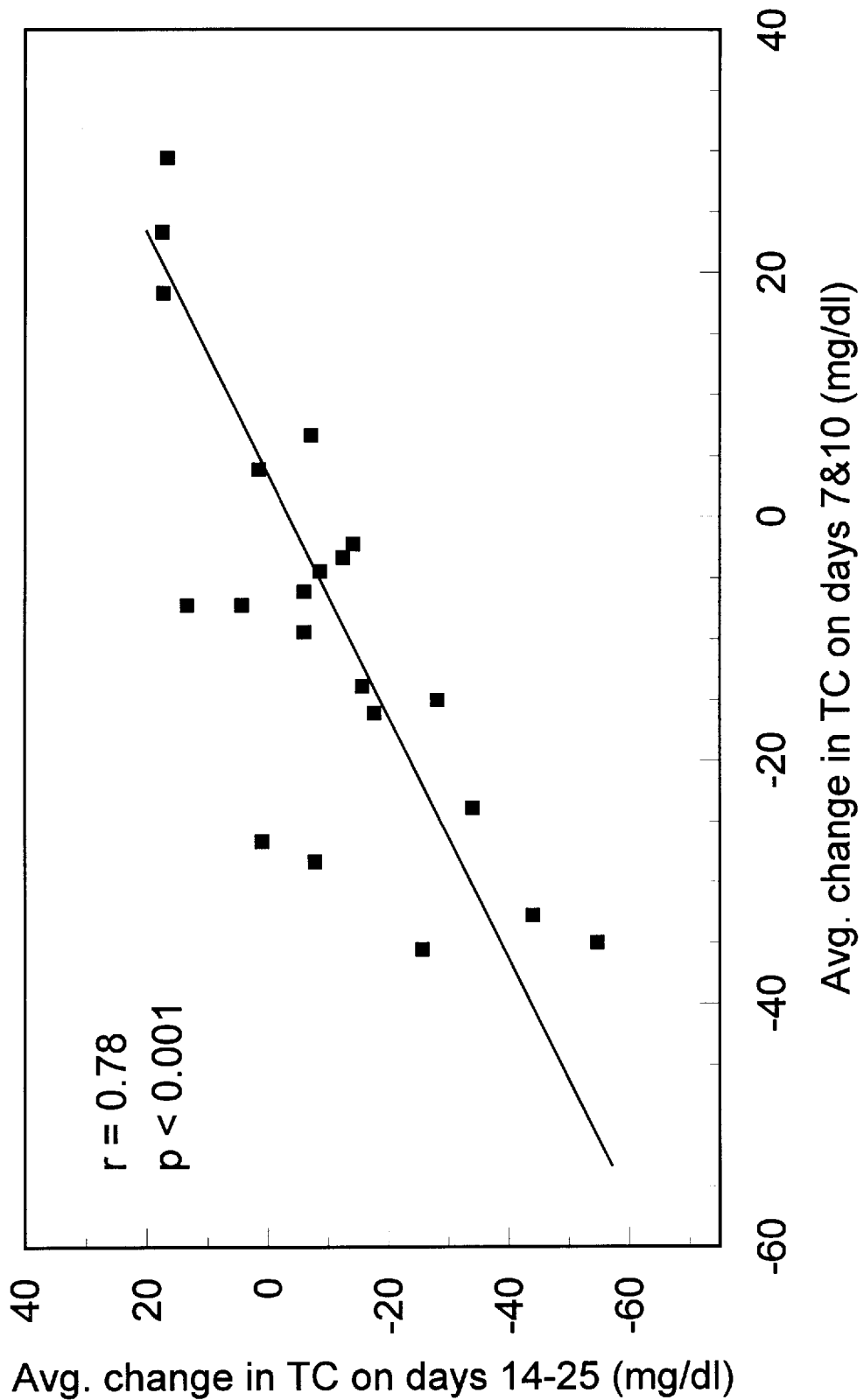
FIGS. 2 and 5 plot the relationship between average early change in total cholesterol (on days 7 to 10) against the average later change in total cholesterol (on days 14 to 25) in subjects consuming fortified, low-fat nutritional products according to the invention, as described in more detail in examples I and II.

Additionally, the predictive value of the 50% Ensure High Protein diet over the full range of cholesterolemic responses was determined by plotting the relationship between early TC response and final TC response in the 50% diet group. As shown in FIG. 2, the relationship between average change in total cholesterol (mg/dL) on days 7 to 10 and average change in total cholesterol (mg/dL) on days 14 to 25 in subjects (n=21) consuming Ensure High Protein were significantly correlated with r=0.782 (p<0.001).

Figure 3:
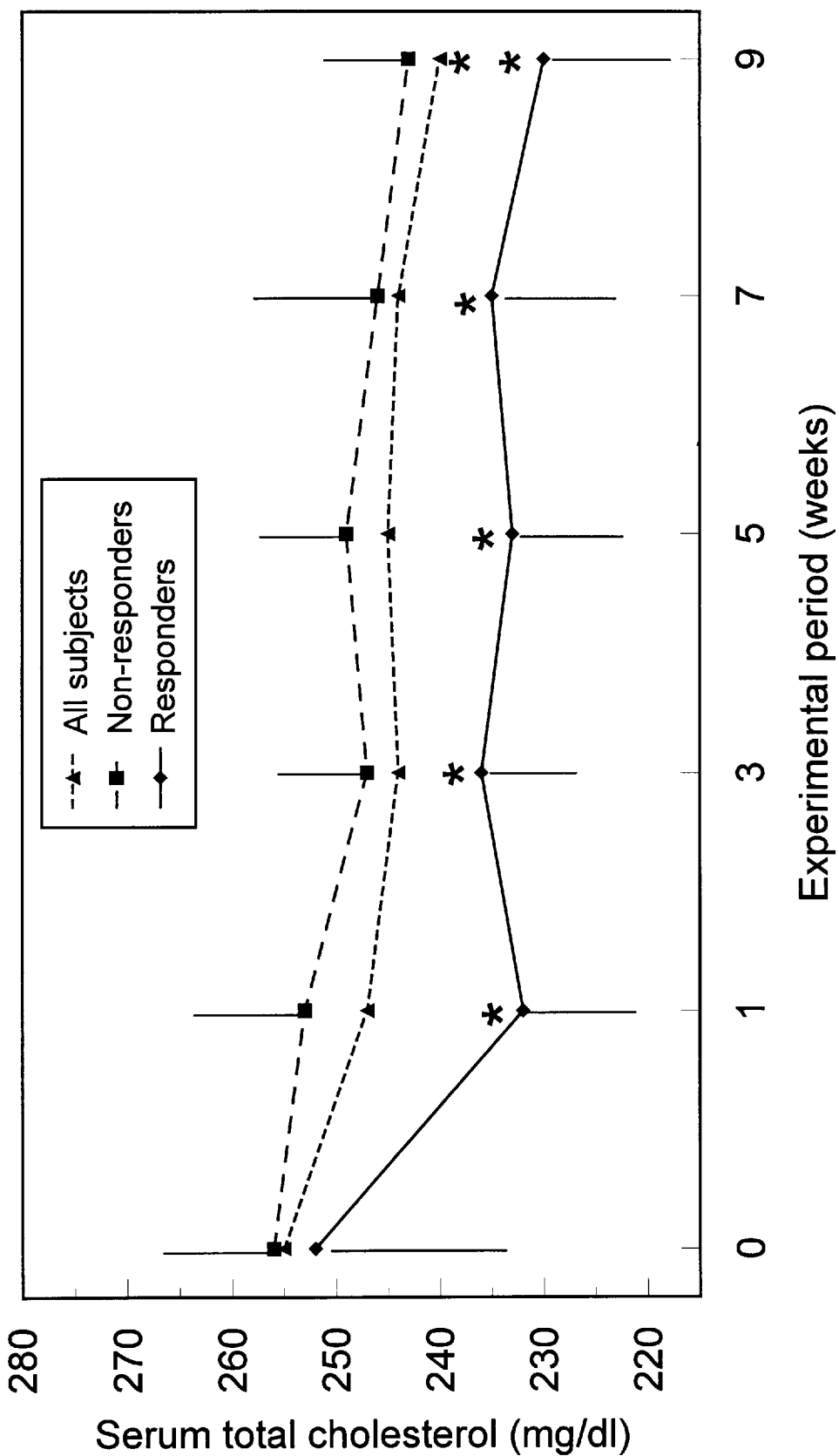
FIGS. 3 and 6 describe the changes in serum total cholesterol in the experimental groups of Examples I and II, respectively, during the 9 week follow-up period during which individuals self selected foods according to a Step I diet. The correlation between the early term predictions and the later follow-up period illustrate the method of the invention.

At the completion of the 50% Ensure High Protein diet experimental phase, subjects returned to their normal diet for several weeks. After this return to their baseline diet, they were asked to follow a Step I Diet for a period of 9 weeks. The rational for this period of the study was to determine whether the changes observed during the 50% diet period would approximate the changes obtained when following a self selected Step I solid food diet. The subjects attended three presentations on cholesterol-lowering diet modification and had two private consultations with a dietitian to answer questions. Fasting serum samples were taken at day 0 and after 1, 3, 5, 7 and 9 weeks. Overall there was a modest reduction in serum lipids over the 9 weeks of self-selected Step I diet [FIG. 3, responders, n=5 (♦); non-responders, n=16 (■); Ensure High Protein group, n=21 (▲)]. When the 5 responders were considered separately it is obvious that they were much more responsive to a cholesterol-lowering Step I Diet than were the previously identified non-responders.

EXAMPLE II

Hypercholesterolemic subjects who were candidates for cholesterol-lowering dietary intervention, according to national Cholesterol Education Program (NCEP) criteria, replaced 100% of their total calories with a complete liquid nutritional (Study BG34-II ). The purpose of the present study was to determine whether a diet of 100% liquid nutritional which meets the NCEP guidelines could distinguish between low-fat diet "responders" and "non-responders" in a 14 day period.

Thirty subjects (13 women and 17 men) between the ages of 21 and 70 were selected from screening sessions. Inclusion and exclusion criteria were the same as for Example I. Twenty-two subjects were fed a diet composed of 100% of calories from a complete liquid nutritional. The complete liquid nutritional was a modified version of commercial Ensure with Fiber. The product composition is listed in Table 4, below.

Product was manufactured according to the Bill of Materials (Table 4) using the method set forth below. A protein-in-water slurry (PIW) is prepared by adding the specified amount of sodium and calcium caseinate to the appropriate amount of heated water and agitating until the protein is dissolved. The PIW slurry is held under agitation until used. A carbohydrate/mineral slurry (CHO/MIN) is prepared by adding the stabilizer and minerals to the appropriate amount of heated water and agitating for five minutes. Add the Lodex 15 and sucrose to the mixture and agitate thoroughly. Add the Softex oat fiber and Fibrim 300 soy fiber and mix well. Maintain the CHO/MIN slurry under agitation until used.

A protein-in-fat slurry is prepared by placing the specified amounts of high oleic safflower oil, canola oil and corn oil in a tank and heating the oil blend to a temperature in the range of 120–125 degrees F. under agitation. The specified amounts of the emulsifiers and oil soluble vitamins are added to the oil blend. The specified amount of soy protein isolate is added to the oil blend under agitation (PIF) and held until used.

A blend is prepared by adding the PIW, CHO/MIN and PIF in a blend tank under agitation. Use 1.0N potassium hydroxide to adjust the pH of the blend to be in the range of 6.6 to 6.9. The blend is subjected to Ultra High Temperature Short Time (UHTST) heat treatment, homogenization and cooled to 38 to 44 degrees F.

Prepare an ascorbic acid solution by adding the specified amount of ascorbic acid to an appropriate amount of water and adjust the pH with 45% potassium hydroxide to a range of 6 to 10 and add to the cooled blend.

Prepare the water soluble vitamin slurry by adding the specified amount of water soluble vitamins to an appropriate amount of water and add to the cooled blend.

Dilute the blend with the necessary amount of water to bring the percent of total solids content, fat and protein to be within the desired ranges. Place the blend in suitable containers and then sterilize the product.

TABLE 4

Modified Ensure with Fiber Composition

| INGREDIENT | QUANTITY % |
|---|---|
| INGREDIENT WATER | 74.19 |
| LODEX 15 | 9.83 |
| SUCROSE | 6.22 |
| CALCIUM & SODIUM CASEINATES | 2.93 |
| SOFTEX OAT FIBER | 1.29 |
| HIGH OLEIC SAFFLOWER OIL | 0.86 |

TABLE 4-continued

Modified Ensure with Fiber Composition

| INGREDIENT | QUANTITY % |
|---|---|
| CANOLA OIL | 0.86 |
| COCOA POWDER | 0.8 |
| SOY PROTEIN ISOLATE | 0.76 |
| CORN OIL | 0.43 |
| FIBRIM 300 SOY FIBER | 0.39 |
| TRICALCIUM PHOSPHATE | 0.29 |
| MAGNESIUM CHLORIDE | 0.25 |
| DIPOTASSIUM PHOSPHATE | 0.13 |
| ART. VANILLA | 0.11 |
| SODIUM CITRATE | 0.1 |
| POTASSIUM CITRATE | 0.1 |
| PANODAN 150SK | 0.09 |
| DIMODAN PVK | 0.09 |
| MONO- AND DI-GLYCERIDES | 0.06 |
| CHOLINE CHLORIDE | 0.05 |
| MAGNESIUM PHOSPHATE | 0.04 |
| ASCORBIC ACID | 0.04 |
| POTASSIUM CHLORIDE | 0.03 |
| CARRAGEENAN | 90 |
| FERROUS SULFATE, MONOHYDRATE | 59.3 |
| ALPHA-TOCOPHERYL ACETATE | 52.66 |
| ZINC SULFATE, MONOHYDRATE | 45.59 |
| NIACINAMIDE | 25.75 |
| MANGANESE SULFATE, MONOHYDRATE | 16.85 |
| CALCIUM PANTOTHENATE | 16.65 |
| GUAR GUM | 15 |
| CUPRIC SULFATE, PENTAHYDRATE | 8.74 |
| VITAMIN A PALMITATE | 8.41 |
| THIAMINE CHLORIDE HYDROCHLORIDE | 4.25 |
| PYRIDOXINE HYDROCHLORIDE | 4.09 |
| RIBOFLAVIN | 3.32 |
| FOLIC ACID | 0.58 |
| SODIUM MOLYBDATE, DIHYDRATE | 0.56 |
| BIOTIN | 0.5 |
| SODIUM SELENATE, ANHYDROUS | 0.44 |
| CHROMIUM CHLORIDE, HEXAHYDRATE | 0.2 |
| POTASSIUM IODIDE | 0.2 |
| PHYLLOQUINONE | 0.09 |
| CYANOCOBALAMIN | 0.01 |
| VITAMIN D3 | 0.01 |

The manufactured product was fed to subjects based on caloric need. Caloric need was determined by the Harris-Benedict formula, modified for activity. No fewer than seven cans were consumed per day. A reference group (N=8) continued consuming their normal diet. Fasting serum lipids and body weight were measured at day 0, 3, 5, 7, 10, and 14 in the twenty-two subjects consuming 100% liquid nutritional. In the eight reference subjects, fasting serum lipids were measured at days 0, 10 and 14. Fasting serum lipids measurements were made as in Example I.

In contrast to the reference group, patients consuming 100% liquid nutritional product had a consistent and significant reduction in serum lipids at several time points over the 14 day experimental period when compared to pre-diet intervention serum lipid levels. Overall, there was a 9.4% (average 25 mg/dL) reduction in TC (p=0.003) and HDL-C decreased 4.5 mg/dL (p=0.001) compared to pre diet intervention.

Figure 4:
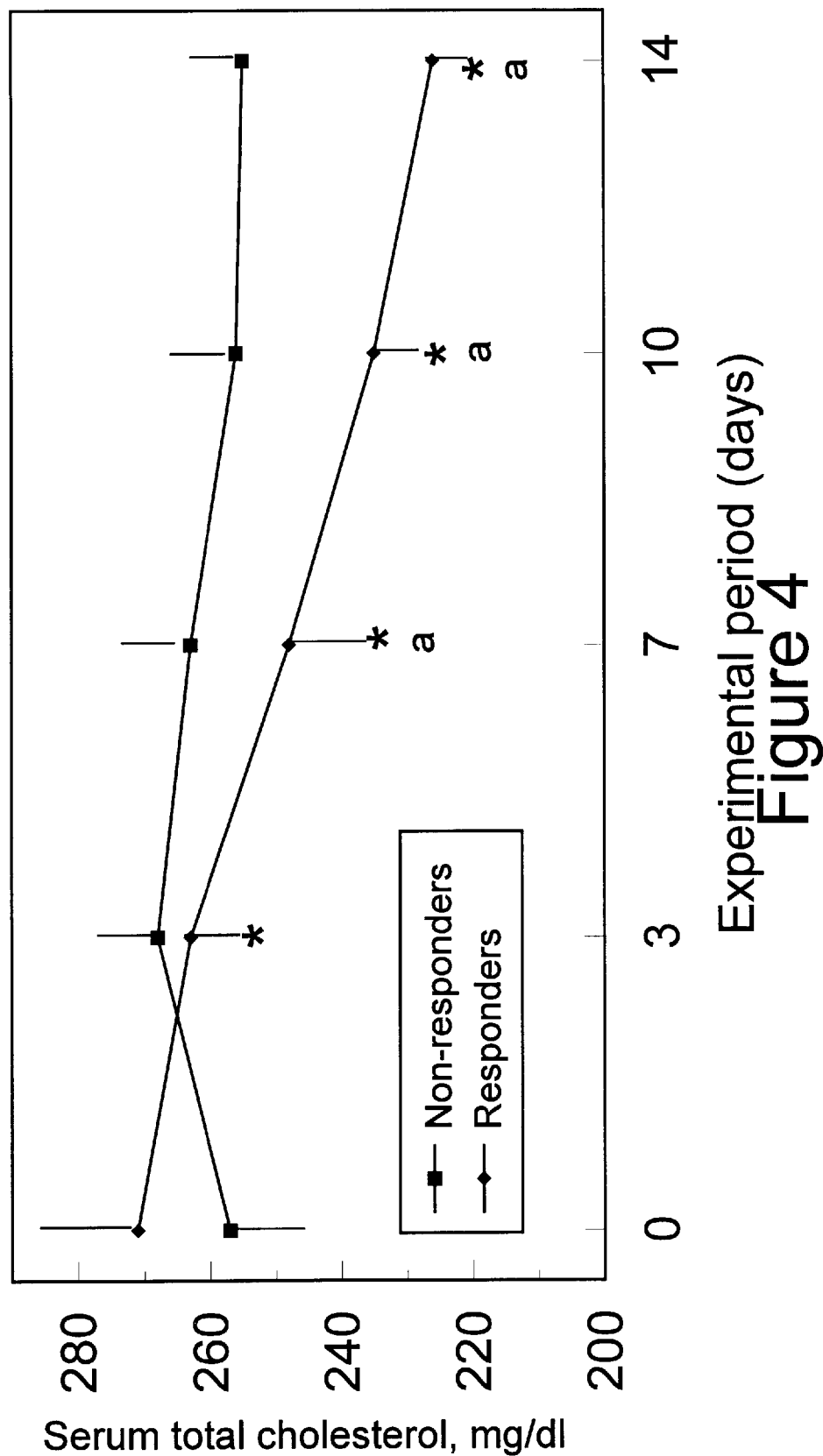

"Responders", defined as in Example I (i.e. meeting target level of 10% or more decrease from baseline), comprised 12 of the 22 (55%) 100% diet subjects. The group of responders achieved a decrease in serum TC greater than 10% by day 7 and the decrease continued until the end of the study. Eight of the 12 responders had a greater than 10% decrease in their TC levels by day 10 resulting in a 66% correct identification of responders. Changes in total cholesterol (mg/dL) levels in responders, n=12 (■) and non-responders, n=10 (♦) over a 14 day period of consuming 100% of total calories as a complete nutritional are plotted in FIG. 4. [*=significantly different compared to day 0 (p<0.05); a=significantly different compared to non-responsive group (p <0.05)]. The mean change in serum cholesterol levels in the remaining 10 "non-responders" (45%) did not change significantly (average 0.1%, ns) over the 14 days (100% correct identification). The 100% liquid nutritional diet correctly identify 66% of the responders and 100% of the non-responders by day 10, using 2 separate fasting serum cholesterol values.

TABLE 5

Number of Patients Correctly Identified

| | Early TC response avg. 7 and 10 day value | Final TC response after 14 day valued | Accuracy |
|---|---|---|---|
| Responders (n = 12) | 8 | 12 | 66% |
| Non-responders (n = 10) | 10 | 10 | 100% |

Figure 5:
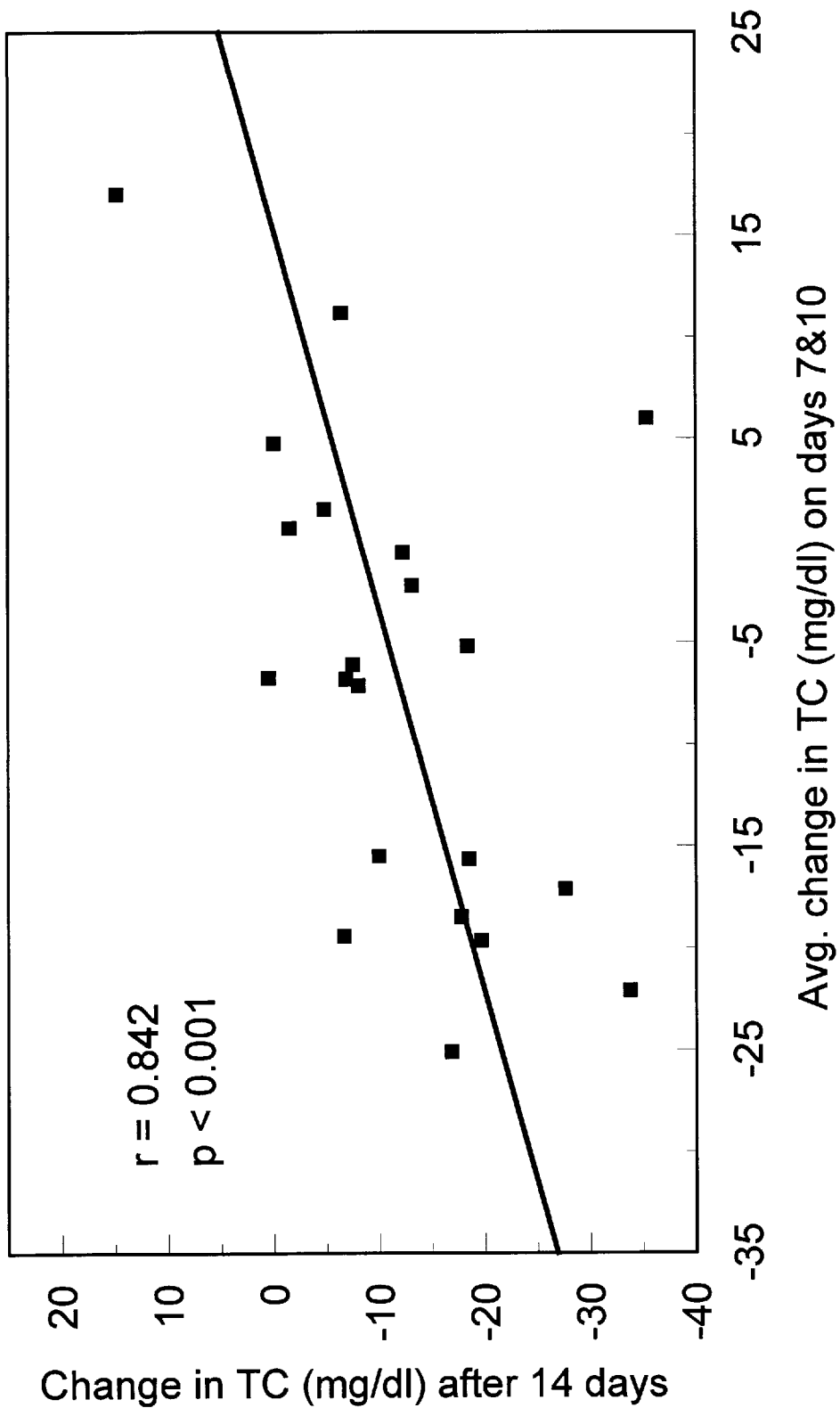

Additionally, the predictive value of the 100% diet over the full range of cholesterolemic responses was determined by plotting the relationship between early TC response and final TC response in the entire 100% liquid nutritional group. As shown in FIG. 5, the relationship between average change in total cholesterol (mg/dL) on days 7 to 10 and average change in total cholesterol (mg/dL) on day 14 in subjects (n=21) consuming 100% complete nutritional product were significantly correlated with r=0.842 (p<0.001).

Figure 6:
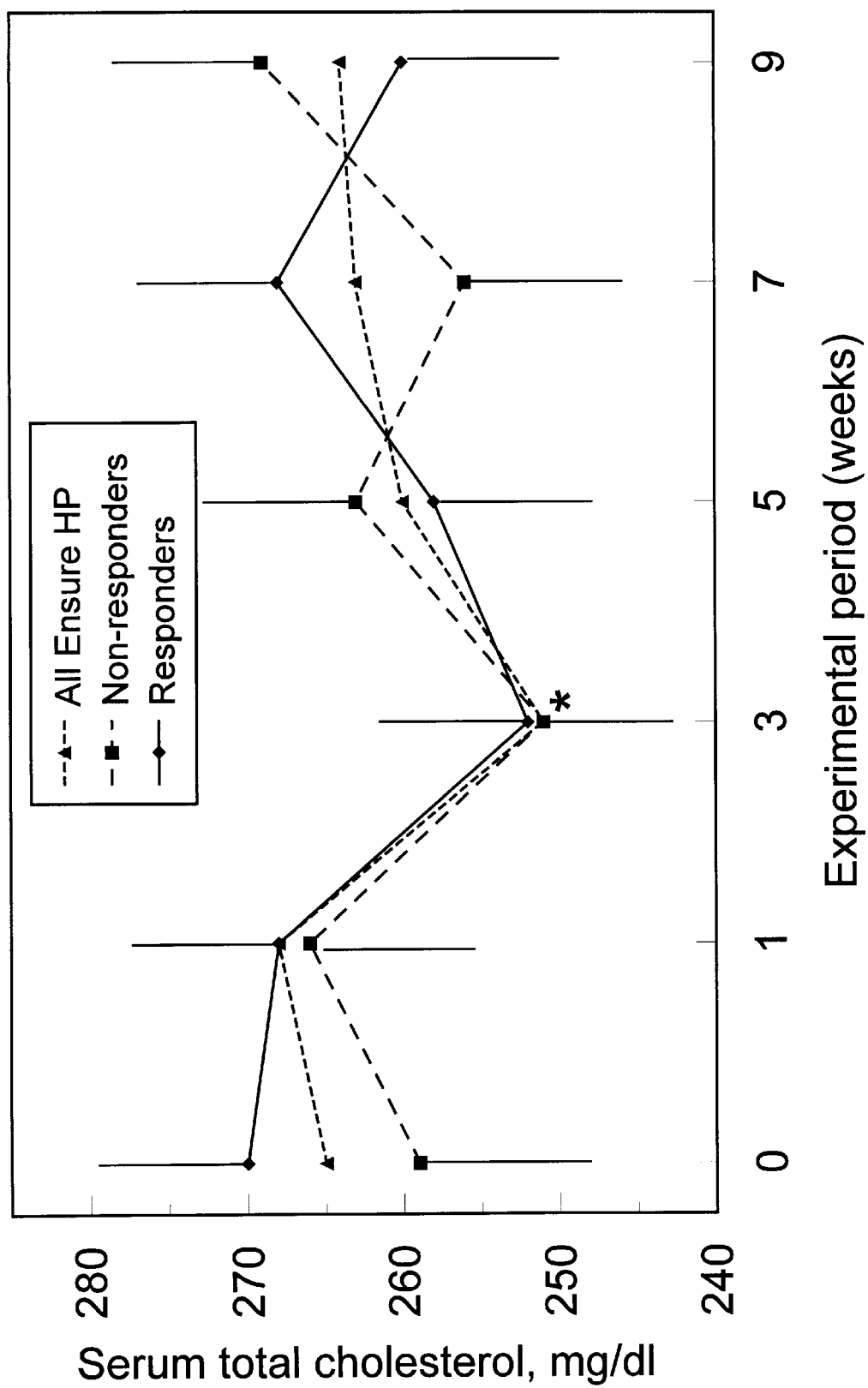

At the completion of the 100% diet experimental phase, subjects returned to their normal diet for several weeks. After this return to their baseline diet, they were asked to follow a Step I diet for a period of 9 weeks. The rational for this period of the study was to determine whether the changes observed during the 100% diet period would approximate the changes obtained when following the self-selected Step I Diet. The subjects attended three presentations on cholesterol-lowering diet modification and had two private consultations with a dietitian to answer questions. Fasting serum samples were taken at day 0 and after 1, 3, 5, 7 and 9 weeks. It was apparent that there was a great deal of variation in serum cholesterol throughout this follow-up phase of the study. When the 12 responders were considered separately it appears that they were slightly more responsive to a cholesterol-lowering Step I Diet than the 12 non-responders. By the end of the 9 week period, the non-responders had an overall 4% increase in TC while the responders had a 4% decrease in serum TC, compared to pre-diet modification. The changes in serum cholesterol (mg/dL) in the 100% complete nutritional product group during the 9 week self selected Step I diet period are plotted in FIG. 6 [responders, n=12 (■); non-responders, n=9 (♦); 100% defined complete nutritional group, n=21 (●)].

CONCLUSION

Two examples of this invention discussed above accomplished the goal of providing a convenient, rapid, accurate and economical way to predict a hypercholesterolemic person's serum cholesterol response to a low fat diet. Each of the methods described in the Examples have inherent advantages and disadvantages. The 50% diet application promoted the adoption of healthy eating patterns by requiring the consumption of self-selected fruits, vegetables and nonfat dairy and grain products. However, the consumption of self-selected foods may increase the potential for noncompliance. The 100% diet application omits the obligation to self-selected foods which decreases the possibility of non-compliance. However, a sole source diet is harder to follow and may be less desirable in a otherwise "healthy population".

What is claimed is:

1. A method of predicting within about 3 to about 25 days the long term serum cholesterol response to a low-fat diet in a hypercholesterolemic person, said method comprising:
   (a) measuring said person's baseline serum total cholesterol concentration;
   (b) defining a target serum total cholesterol concentration for said person, said target being defined in accordance with NCEP guidelines:
   (c) feeding said hypercholesterolemic person a diet that is a NCEP Step I Diet for a term of about 3 to about 25 days; wherein about 50 to 100% of the caloric intake of said person is supplied by a fortified, low-fat nutritional product; and
   (d) at the end of said term, measuring said person's serum total cholesterol concentration and comparing it to the baseline concentration; wherein a decrease in total cholesterol to a concentration at or below said defined target concentration is predictive of favorable response to dietary intervention.

2. The method of claim 1 wherein the term is about 3 to about 14 days.

3. The method of claim 1 wherein the term is about 5 to about 10 days.

4. The method of claim 1 wherein said target serum total cholesterol concentration is defined as a decrease of about 10% or more from baseline concentration of said person.

5. The method of claim 1 wherein 100% of said person's caloric intake is from said fortified, low-fat nutritional product.

6. The method of claim 1 wherein less than 100% of said person's caloric intake is from said fortified, low-fat nutritional product and the remaining caloric intake is from conventional foods recommended in NCEP Step I guidelines.

7. The method of claim 1 wherein said fortified, low-fat nutritional product is a liquid having a caloric density of about 0.2 kcal/ml to about 2.0 kcal/ml.

8. The method of claim 1 wherein said fortified, low-fat nutritional product is a solid having a caloric density of about 75 kcal/oz to about 150 kcal/oz.

9. A method of identifying within about 3 to about 25 days a hypercholesterolemic person who will fail to respond to a low-fat diet designed to lower serum total cholesterol, said method comprising:
   (a) measuring said person's baseline serum total cholesterol concentration;
   (b) defining a target serum total cholesterol concentration for said person, said target being defined in accordance with NCEP guidelines;
   (c) feeding said hypercholesterolemic person a diet that is a NCEP Step I Diet for a term of about 3 to about 25 days; wherein about 50 to 100% of the caloric intake of said person is supplied by a fortified, low-fat nutritional product; and
   (d) at the end of said term, measuring said person's serum total cholesterol concentration and comparing it to the baseline concentration; wherein a failure to achieve a serum total cholesterol concentration at or below said target concentration is indicative of a person who will fail to respond to dietary intervention.

10. The method of claim 9 wherein the term is about 3 to about 14 days.

11. The method of claim 9 wherein the term is about 5 to about 10 days.

12. The method of claim 9 wherein said target serum total cholesterol concentration is defined as a decrease of about 10% or more from baseline concentration of said person.

13. The method of claim 9 wherein 100% of said person's caloric intake is from said fortified, low-fat nutritional product.

14. The method of claim 9 wherein less than 100% of said person's caloric intake is from said fortified, low-fat nutritional product and the remaining caloric intake is from conventional foods recommended in NCEP Step I guidelines.

15. The method of claim 9 wherein said fortified, low-fat nutritional product is a liquid having a caloric density of about 0.2 kcal/ml to about 2.0 kcal/ml.

16. The method of claim 9 wherein said fortified, low-fat nutritional product is a solid having a caloric density of about 75 kcal/oz to about 150 kcal/oz.

17. A method of identifying within about 3 to about 25 days a hypercholesterolemic person who is likely to respond to dietary intervention with a conventional low-fat diet, said method comprising:
   (a) measuring said person's baseline serum total cholesterol concentration;
   (b) defining a target serum total cholesterol concentration for said person, said target being defined in accordance with NCEP guidelines;
   (c) feeding said hypercholesterolemic person a diet that is a NCEP Step I Diet for a term of about 3 to about 25 days; wherein about 50 to 100% of the caloric intake of said person is supplied by a fortified, low-fat nutritional product; and
   (d) at the end of said term, measuring said person's serum total cholesterol concentration and comparing it to the baseline concentration; wherein a decrease in total cholesterol to a concentration at or below said defined target concentration is indicative of a person likely to respond to dietary intervention.

18. The method of claim 17 wherein the term is about 3 to about 14 days.

19. The method of claim 17 wherein the term is about 5 to about 10 days.

20. The method of claim 17 wherein 100% of said person's caloric intake is from said fortified, low-fat nutritional product.

21. The method of claim 17 wherein less than 100% of said person's caloric intake is from said fortified, low-fat nutritional product and the remaining caloric intake is from conventional foods recommended in NCEP Step I guidelines.

22. The method of claim 17 wherein said target serum total cholesterol concentration is defined as a decrease of about 10% or more from baseline concentration of said person.

23. A method of identifying within about 3 to about 25 days those hypercholesterolemic persons who are candidates for drug therapy with cholesterol-lowering drugs, said method comprising:
   (a) measuring said person's baseline serum total cholesterol concentration;
   (b) defining a target serum total cholesterol concentration for said person, said target being defined in accordance with NCEP guidelines;
   (c) feeding said hypercholesterolemic person a diet that is a NCEP Step I Diet for a term of about 3 to about 25 days; wherein about 50 to 100% of the caloric intake of said person is supplied by a fortified, low-fat nutritional product; and (d) at the end of said term, measuring said person's serum total cholesterol concentration and comparing it to the baseline concentration; wherein a decrease in total cholesterol to a concentration at or below said defined target concentration is indicative of a candidate for drug therapy.

24. The method of claim 23 wherein the term is about 3 to about 14 days.

25. The method of claim 23 wherein the term is about 5 to about 10 days.

26. The method of claim 23 wherein 100% of said person's caloric intake is from said fortified, low-fat nutritional product.

27. The method of claim 23 wherein less than 100% of said person's caloric intake is from said fortified, low-fat nutritional product and the remaining caloric intake is from conventional foods recommended in NCEP Step I guidelines.

28. The method of claim 23 wherein said target serum total cholesterol concentration is defined as a decrease of about 10% or more from baseline concentration of said person.

* * * * *

UNITED STATES PATENT AND TRADEMARK OFFICE
CERTIFICATE OF CORRECTION

PATENT NO. : 5,891,925
DATED : April 6, 1999
INVENTOR(S) : Behr

Page 1 of 1

It is certified that error appears in the above-identified patent and that said Letters Patent is hereby corrected as shown below:

Claim 23,
Part (d) should read:
(d) At the end of said term, measuring said person's serum total cholesterol concentration and comparing it to the baseline concentration; wherein a failure to decrease total cholesterol to a concentration at or below said defined target concentration is indicative of a candidate for drug therapy Title page, Item [54], and Column 1, Lines 1-4,
Should read:
DIAGNOSTIC METHOD FOR ASSESSING THE SERUM CHOLESTEROL RESPONSE TO LOW FAT DIETS Signed and Sealed this Eighteenth Day of September, 2001

Attest:

NICHOLAS P. GODICI
Attesting Officer
Acting Director of the United States Patent and Trademark Office

UNITED STATES PATENT AND TRADEMARK OFFICE
CERTIFICATE OF CORRECTION

PATENT NO. : 5,891,925
DATED : April 6, 1999
INVENTOR(S) : Behr

It is certified that error appears in the above-identified patent and that said Letters Patent is hereby corrected as shown below:

In the Claims,
Claim #23 part (d) should read:
(d) at the end of said term, measuring said person's serum total cholesterol concentration and comparing it to the baseline concentration; wherein a failure to decrease total cholesterol to a concentration at or below said defined target concentrtation is indicative of a candidate for drug therapy Title should read:

DIAGNOSTIC METHOD FOR ASSESSING THE SERUM CHOLESTEROL RESPONSE TO LOW FAT DIETS

Signed and Sealed this

Twenty-third Day of October, 2001

*Attest:*

NICHOLAS P. GODICI
*Attesting Officer*    Acting Director of the United States Patent and Trademark Office